(12) United States Patent
Sprecker et al.

(10) Patent No.: US 7,407,928 B2
(45) Date of Patent: Aug. 5, 2008

(54) SOLID PHASE BENZOPYRAN COMPOSITION, PROCESS FOR PREPARING SAME AND ORGANOLEPTIC USES THEREOF

(75) Inventors: Mark A. Sprecker, Sea Bright, NJ (US); Robert P. Belko, Monroe, NJ (US); Bruce Mechanic, Colts Neck, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 612 days.

(21) Appl. No.: 10/361,748

(22) Filed: Feb. 10, 2003

(65) Prior Publication Data

US 2004/0157764 A1    Aug. 12, 2004

(51) Int. Cl.
*A61K 8/18*    (2006.01)
*C07C 15/00*    (2006.01)
(52) U.S. Cl. ............... 512/14; 512/13; 585/410
(58) Field of Classification Search .......... 512/14, 512/13, 17; 568/808, 659; 570/183; 549/359; 585/410
See application file for complete search history.

(56) References Cited

U.S. PATENT DOCUMENTS

| | | | |
|---|---|---|---|
| 3,360,530 A | | 12/1967 | Heeringa et al. |
| 4,265,818 A | | 5/1981 | Wiegers et al. |
| 4,301,076 A | * | 11/1981 | Wiegers et al. ............. 549/385 |
| 4,308,412 A | * | 12/1981 | Wiegers et al. ............. 585/410 |
| 4,650,603 A | | 3/1987 | Sprecker |
| 5,376,630 A | | 12/1994 | Sprecker et al. |
| 5,494,892 A | * | 2/1996 | Sprecker et al. ............... 512/14 |
| 5,502,031 A | * | 3/1996 | Sprecker et al. ............... 512/13 |
| 5,635,471 A | | 6/1997 | Frater et al. |
| 6,090,774 A | | 7/2000 | Moscona et al. |

FOREIGN PATENT DOCUMENTS

EP    1 061 125 A2    12/2000

OTHER PUBLICATIONS

Frater, et al. II. Helvetica Chimica Acta. vol. 82, 1999, pp. 1656-1665.

* cited by examiner

*Primary Examiner*—Jill Warden
*Assistant Examiner*—Keri A Moss
(74) *Attorney, Agent, or Firm*—Elizabeth M. Quirk; Xufan Tseng; Joseph F. Leightner

(57) ABSTRACT

Described is a solid phase benzopyran composition comprising predominately 1,3,4,6,7,8-hexahydro-4,6,6,7,8,8-hexamethylcyclopenta[G]-2-benzopyran and at least one other benzopyran compound. The novel compositions are used in augmenting, enhancing and/or imparting aromas in to consumable materials such as perfume compositions, perfumed articles including soaps, detergents, fabric softener compositions, fabric softener articles, fragranced candles, cosmetics, hair preparations, perfumed polymers and colognes. Also described is a process for producing the solid phase benzopyran compositions.

9 Claims, 2 Drawing Sheets

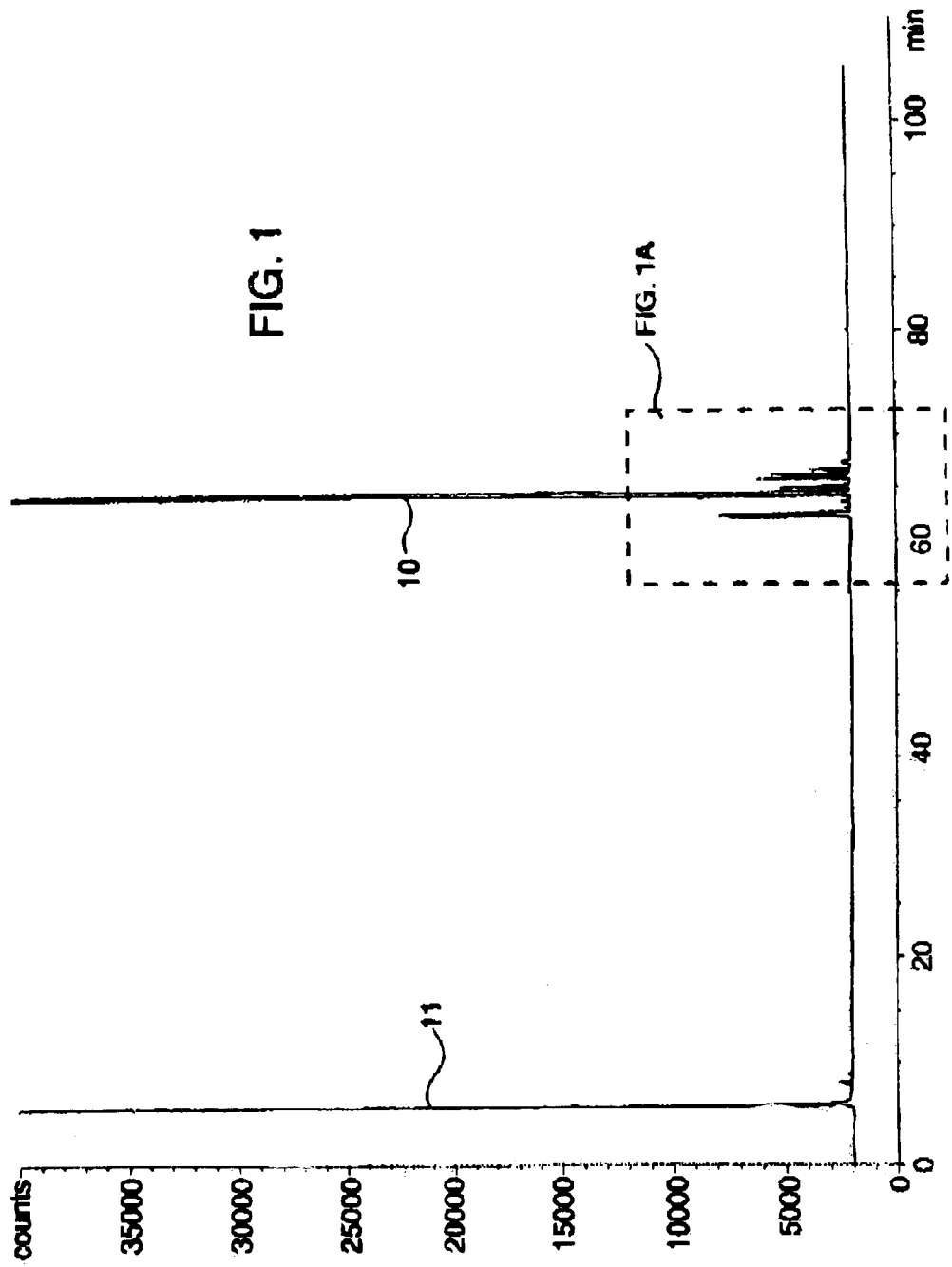

SOLID PHASE BENZOPYRAN COMPOSITION, PROCESS FOR PREPARING SAME AND ORGANOLEPTIC USES THEREOF

FIELD OF THE INVENTION

The invention relates to a novel solid phase fragrance product comprised of predominately 1,3,4,6,7,8-hexahydro-4,6,6,7,8,8-hexamethylcyclopenta[G]-2-benzopyran and further comprising additional benzopyran materials. The fragrance product can be used in perfume compositions and consumer products.

BACKGROUND OF THE INVENTION

The liquid phase benzopyran composition containing from 70-81% by weight of 1,3,4,6,7,8-hexahydro-4,6,6,7,8,8-hexamethylcyclopenta[G]-2-benzopyran having the structure:

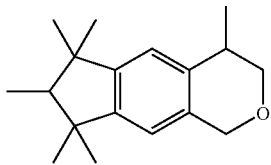

(known as "GALAXOLIDE 100", registered trademark of International Flavors & Fragrances Inc. of New York, N.Y.) and solutions thereof, for example, 50% solutions in diethyl phthalate (known as "GALAXOLIDE 50", registered trademark of International Flavors & Fragrances Inc. of New York, N.Y.) are among the largest volume aroma chemicals currently in use in commerce. The material is known to impart to consumable materials including fine fragrances and perfumes for use in functional products such as soaps and detergents, a tenacious and substantive musk aroma. As manufactured, the liquid phase benzopyran composition known as "GALAXOLIDE" contains 70-75% by weight of 1,3,4,6,7,8-hexahydro-4,6,6,7,8,8-hexamethylcyclopenta[G]-2-benzopyran having the structure:

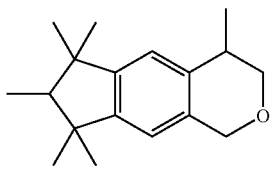

which structure contains four diastereomeric isomers including the 4R-cis and trans isomers and the 4S-cis and trans isomers. Frater et al. I, U.S. Pat. No. 5,635,471, the specification of which is herein incorporated by reference, discloses that the mixture of the 7R and 7S diastereoisomers have a stronger musk aroma and Frater et al. II, Helvetica Chimica Acta. Vol. 82, 1999, pp. 1656-1665 discloses that the strongest isomer is the (−)-(4S,7R) isomer. GALAXOLIDE as commercially produced and as taught by the art to be produceable, for example, U.S. Pat. No. 3,360,530, the specification for which is herein incorporated by reference, consists of a thick, viscous liquid which can solidify at cold temperatures, for example at 0° C. It is well known to those skilled in the art that this material is difficult to handle either as the highly concentrated viscous liquid or as diluted in a solvent such as diethyl phthalate benzyl benzoate, isopropyl myristate and/or dipropylene glycol. Typically, it is diluted so that the major isomers, indicated by the structure:

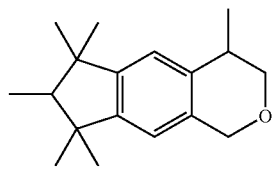

make up 50% of the solution, by weight. As currently manufactured, and as disclosed in the prior art, GALAXOLIDE has been reported to have some adverse environmental effects. Accordingly, a need exists to provide a form of GALAXOLIDE that can be used in perfumes, colognes and perfumed articles in substantially lower dosages than heretofore known in the art, thereby protecting the environment.

Solid forms of GALAXOLIDE are disclosed in the prior art, including
  (a) Sprecker, U.S. Pat. No. 4,650,603, the disclosure of which is herein incorporated by reference; and
  (b) Frater et al. II, U.S. Pat. No. 5,635,471.

However, the solid forms of GALAXOLIDE so disclosed in the prior art do not contain the necessary and desirable high percentages, 85-95 weight % of the isomers having the structure:

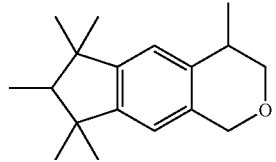

which high percentages cause the solid phase benzopyran compositions of our invention to have unobvious, unexpected and advantages organoleptic properties regarding aroma quality, strength and substantivity.

SUMMARY OF THE INVENTION

We have discovered a novel form of a mixture of benzopyran isomers which in the form of a granular, white powdery substance have surprisingly easy handling capabilities. Accordingly, the novel composition of our invention is easily dosed into fragrance formulations. Compared to the currently used forms of GALAXOLIDE, substantially lesser quantities of the novel solid phase benzopyan compositions of our invention are required to provide the same organoleptic musk nuances as provided by the higher amounts of the prior art benzopyran compositions currently used. Accordingly, as a result of the commercial use of the compositions of our invention, and replacement of prior art benzopyran compositions with the solid phase benzopyran compositions of our invention, emissions to the environment of benzopyrans will be significantly reduced.

More specifically, our invention is directed to a solid phase benzopyran composition consisting essentially of from about 85 weight % up to about 95 weight % of 1,3,4,6,7,8-hexahydro-4,6,6,7,8,8-hexamethylcyclopenta[G]-2-benzopyran having the structure:

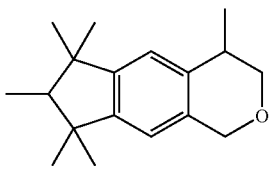

and further comprising at least one benzopyran selected from the group consisting of
(a) 1,3,4,6,7,8-hexahydro-6-ethyl-4,6,8,8-tetramethylcyclopenta[G]-2-benzopyran having the structure:

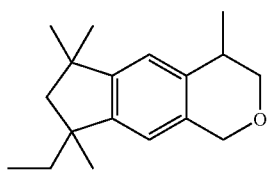

(b) 1,3,4,6,7,8-hexahydro-8-ethyl-4,6,6,8-tetramethylcyclopenta[G]-2-benzopyran having the structure:

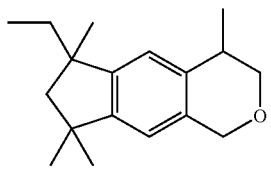

(c) 1,3,4,7,8,9-hexahydro-7-ethyl-4,7,9,9-tetramethylpentamethylcyclopenta[H]-2-benzopyran having the structure:

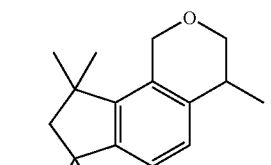

(d) 1,3,4,7,8,9-hexahydro-9-ethyl-4,7,7,9-tetramethylpentamethylcyclopenta[H]-2-benzopyran having the structure:

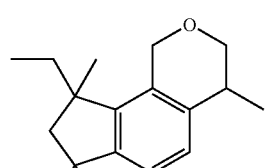

(e) 1,2,4,7,8,9-hexahydro-1,7,7,8,9,9-hexamethylpentamethylcyclopenta[F]-2-benzopyran having the structure:

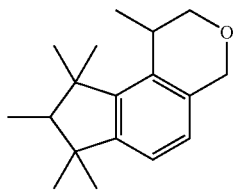

(f) 1,3,4,7,8,9-hexahydro-4,7,7,8,9,9-hexamethylpentamethylcyclopenta[H]-2-benzopyran having the structure:

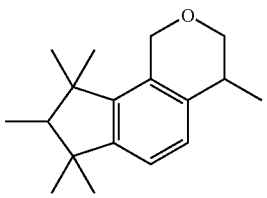

wherein the purity of said solid phase benzopyran mixture is greater than 98% by weight of said mixture.

Preferably, our invention is directed to a solid phase benzopyran composition consisting of:
from about 85 weight % up to about 95 weight % of 1,3,4,6,7,8-hexahydro-4,6,6,7,8,8-hexamethylcyclopenta[G]-2-benzopyran;
from about 2.5 weight % up to about 5.5 weight % of 1,3,4,6,7,8-hexahydro-6-ethyl-4,6,8,8-tetramethylcyclopenta[G]-2-benzopyran;
from about 2.5 weight % up to about 5.5 weight % of 1,3,4,6,7,8-hexahydro-8-ethyl-4,6,6,8-tetramethylcyclopenta[G]-2-benzopyran;
from about 0.2 weight % up to about 0.5 weight % of 1,3,4,7,8,9-hexahydro-7-ethyl-4,7,9,9-tetramethylpentamethylcyclopenta[H]-2-benzopyran;
from about 0.2 weight % up to about 0.5 weight % of 1,3,4,7,8,9-hexahydro-9-ethyl-4,7,7,9-tetramethylpentamethylcyclopenta[H]-2-benzopyran;
from about 2.2 weight % up to about 4.0 weight % of 1,2,4,7,8,9-hexahydro-1,7,7,8,9,9-hexamethylpentamethylcyclopenta[F]-2-benzopyran; and
from about 0.7 weight % up to about 1.3 weight % of 1,3,4,7,8,9-hexahydro-4,7,7,8,9,9-hexamethylpentamethylcyclopenta[H]-2-benzopyran.

The solid phase benzopyran composition of our invention is used in augmenting, enhancing and/or imparting aromas in or to consumable materials, including but not limited to, perfume compositions, perfumed articles including soaps, detergents, fabric softener compositions, and fabric softener articles.

The solid phase benzopyran compositions of our invention are produced according to two alternative processes:

A first process comprising the steps of:
i. admixing a liquid phase benzopyran composition consisting essentially of from about 70 weight % up to about 81 weight % of 1,3,4,6,7,8-hexahydro-4,6,6,7,8,8-hexamethylcyclopenta[G]-2-benzopyran having the structure:

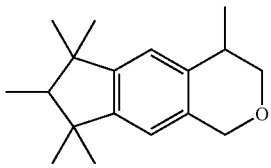

from about 4 weight % up to about 10 weight % of the mixture of compounds (a) 1,3,4,6,7,8-hexahydro-6-ethyl-4,6,8,8-tetramethylcyclopenta[G]-2-benzopyran having the structure:

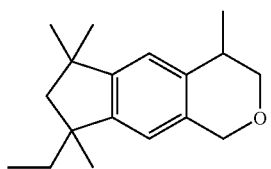

and (b) 1,3,4,6,7,8-hexahydro-8-ethyl-4,6,6,8-tetramethylcyclopenta[G]-2-benzopyran having the structure:

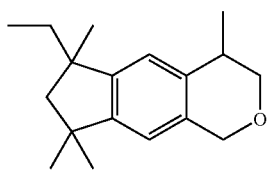

from about 1 weight % up to about 4 weight % of the mixture of the compounds (a) 1,3,4,7,8,9-hexahydro-7-ethyl-4,7,9,9-tetramethylpentamethylcyclopenta[H]-2-benzopyran having the structure:

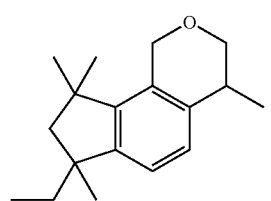

and (b) 1,3,4,7,8,9-hexahydro-9-ethyl-4,7,7,9-tetramethylpentamethylcyclopenta[H]-2-benzopyran having the structure:

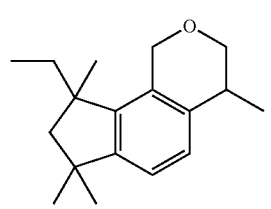

from about 2 weight % up to about 5 weight % of the compound, 1,2,4,7,8,9-hexahydro-1,7,7,8,9,9-hexamethylpentamethylcyclopenta[F]-2-benzopyran having the structure:

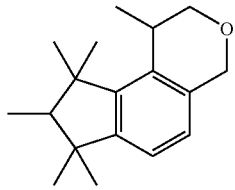

from about 2 weight % up to about 5 weight % of the compound, 1,3,4,7,8,9-hexahydro-4,7,7,8,9,9-hexamethylpentamethylcyclopenta[H]-2-benzopyran having the structure:

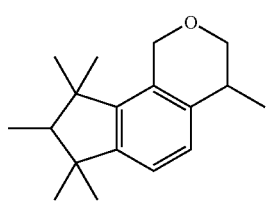

with a compatible solvent which is one or more $C_4$-$C_{10}$ hydrocarbons, for example, toluene, n-octane and n-hexane, lower alkanols, for example, ethyl alcohol, n-propyl alcohol and isopropyl alcohol, lower dialkyl ketones, for example, acetone and methylethyl ketone, lower alkyl lower alkanoates, for example, ethyl acetate, di-lower alkyl ethers, for example, diethyl ether, and lower cyloaliphatic ethers, for example, tetrahydrofuran, the weight percent range of said solvent being from about 20% by weight up to about 80% by weight of said liquid phase benzopyran mixture, thereby forming a liquid phase benzopyran-solvent mixture;

ii. adjusting the temperature of said liquid phase benzopyran-solvent mixture to a temperature in the range of from about −40° C. up to about 0° C. for a solid product-precipitating period of time, for example, 3 hours, thereby forming a mixture of solid phase benzopyran composition and liquid phase benzopyran-solvent mixture, and then iii. separating said solid phase benzopyran composition from said liquid phase benzopyran-solvent mixture, for example, by means of filtration or centrifugation.

A second process comprising the steps of:
i. admixing a liquid phase benzopyran composition consisting essentially of from about 70 weight % up to about 81 weight % of 1,3,4,6,7,8-hexahydro-4,6,6,7,8,8-hexamethylcyclopenta[G]-2-benzopyran;
  from about 4 weight % up to about 10 weight % of the mixture of compounds (a) 1,3,4,6,7,8-hexahydro-6-ethyl-4,6,8,8-tetramethylcyclopenta[G]-2-benzopyran and (b) 1,3,4,6,7,8-hexahydro-8-ethyl-4,6,6,8-tetramethylcyclopenta[G]-2-benzopyran;
  from about 1 weight % up to about 4 weight % of the mixture of the compounds (a) 1,3,4,7,8,9-hexahydro-7-ethyl-4,7,9,9-tetramethylpentamethylcyclopenta[H]-2-benzopyran and (b) 1,3,4,7,8,9-hexahydro-9-ethyl-4,7,7,9-tetramethylpentamethyl-cyclopenta[H]-2-benzopyran;
  from about 2 weight % up to about 5 weight % of the compound, 1,2,4,7,8,9-hexahydro-1,7,7,8,9,9-hexamethylpentamethylcyclopenta[F]-2-benzopyran;
  from about 2 weight % up to about 5 weight % of the compound, 1,3,4,7,8,9-hexahydro-4,7,7,8,9,9-hexamethylpentamethylcyclopenta[H]-2-benzopyran with an aqueous solvent containing from about 2% up to about 20% by weight of water and from about 80% up to about 98% by weight of an organic solvent component which is at least one lower alkanol, for example, ethyl alcohol, isopropyl alcohol and/or n-propyl alcohol, a lower dialkyl ketone, for example, acetone, a lower alkyl lower alkanoate, for example, ethyl acetate, di-ethyl ether and/or tetrahydrofuran, the weight percent range of said aqueous solvent being from about 20% by weight up to about 80% by weight of said liquid phase benzopyran mixture, thereby forming a liquid phase benzopyran-aqueous solvent mixture;

ii. adjusting the temperature of said liquid phase benzopyran-aqueous solvent mixture to a temperature in the range of from about −10° C. up to about 25° C. for a solid product-precipitating period of time, for example, 3 hours, thereby forming a mixture of solid phase benzopyran composition and liquid phase benzopyran-aqueous solvent mixture, and then iii. separating said solid phase benzopyran composition from said liquid phase benzopyran-aqueous solvent mixture, for example, by means of filtration or centrifugation.

The solid phase benzopyran composition of our invention and one or more auxiliary perfume ingredients including, for example, aldehydes, nitriles, esters, cyclic esters, ketones, ethers other than the solid phase benzopyran compositions of our invention, natural essential oils, synthetic essential oils, terpene mercaptans and hydrocarbons may be admixed so that the combined odors of the individual components produces a pleasant and desired fragrance particularly in the musk and "animal-like" fragrance area. The solid phase benzopyran compositions of our invention, even in relatively low concentrations, e.g., 0.005% will impart a sweet, musk "animal-like" aroma to fine fragrances, soaps, anionic, cationic, non-ionic and zwitterionic detergents, fabric softener compositions, fabric softener articles, e.g., BOUNCE® registered trademark of the Procter & Gamble Co. of Cincinnati, Ohio, space odorants and deodorants, sun screens, powders such as talcs, hair preparations and fabric conditioners. Accordingly, the concentration of the solid phase benzopyran composition of our invention taken alone or in admixture with one or more auxiliary perfume ingredients that can be used in fine fragrances or perfumed articles or perfumed polymers can vary from about 0.005% up to about 50% by weight of the fine fragrance or fragranced article preferably from about 0.01 to about 20 and more preferably from about 0.1 weight percent to 10 weight percent. In other embodiments of our invention, the novel compounds of our invention can be incorporated from about 0.005% up to about 5% by weight of the perfumed article, or from about 0.005% up to about 50% by weight of the perfumed article, for example, high density polyethylene as more specifically disclosed in U.S. Pat. No. 6,090,774 the disclosure of which is herein incorporated by reference.

In addition, the perfume composition or fragrance composition of our invention can contain a vehicle or carrier for the solid phase benzopyran composition of our invention, taken alone or further together with one or more auxiliary perfume ingredients. The vehicle can be a liquid such as a non-toxic alcohol, e.g., ethanol, a non-toxic glycol, such as dipropylene glycol, or the like. The carrier can be an absorbent solid such as a gum, including gum arabic, guar gum or carageenan gum or components for microencapsulating the composition using, for example, an encapsulating polymeric matrix such as a polyurethane matrix or a urea-formaldehyde matrix or a modified starch matrix or components for encapsulating the solid phase benzopyran composition particles such as gelatin by means of coacervation.

BRIEF DESCRIPTION OF THE DRAWINGS

FIG. 1 is the GLC profile of the solid phase benzopyran composition produced according to Example I set forth below. (Conditions: 50 meters×0.32 mm.×0.5μ methyl silicone column programmed from 75° C. up to 225° C. at 2° C. per minute)

DETAILED DESCRIPTION OF THE DRAWINGS

Figure 1A:
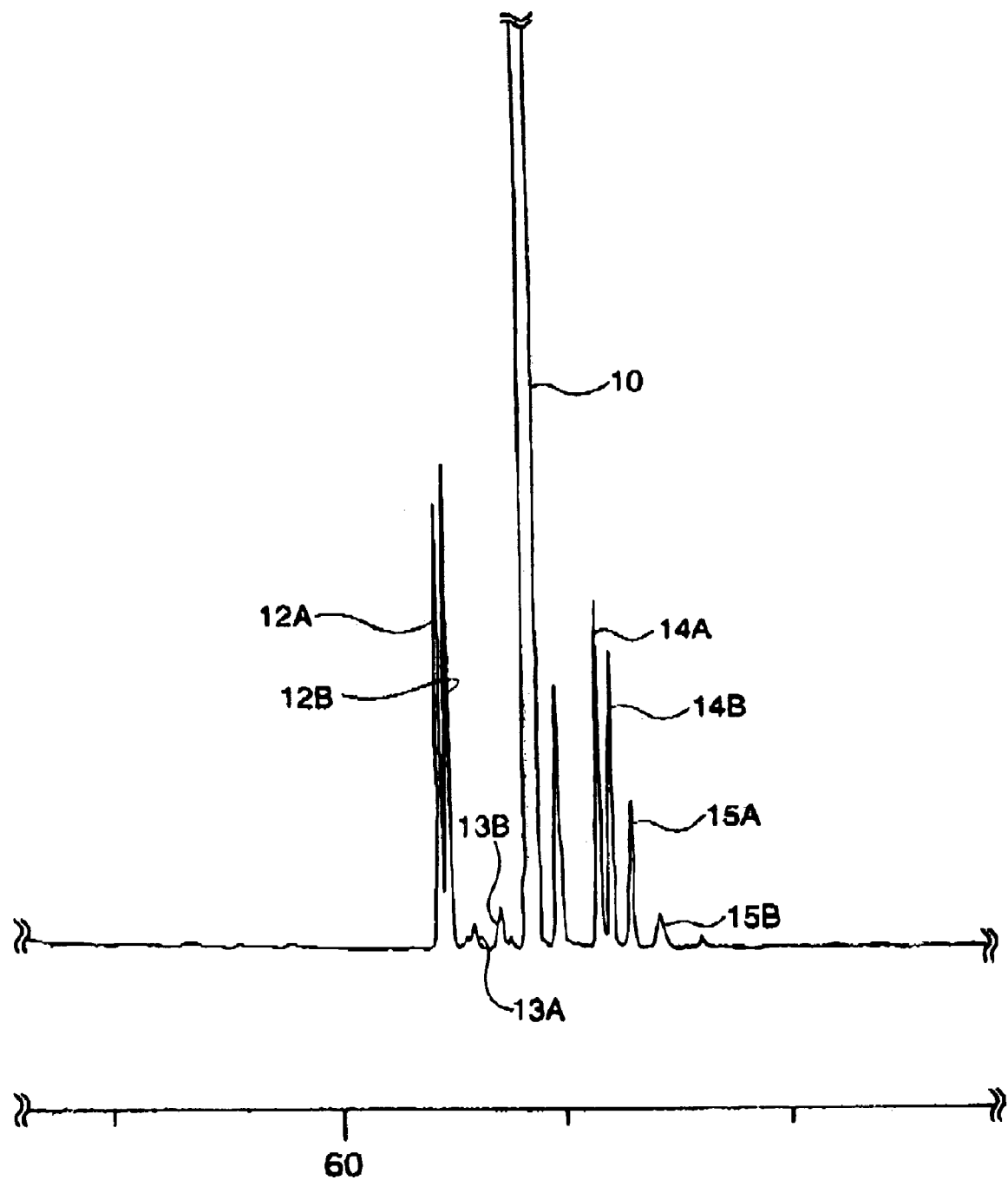
FIG. 1A is an enlargement of the section indicated as "FIG. 1A" on FIG. 1.

Referring to FIG. 1, the peak indicated by reference numeral 10 is for the mixture of diastereomers of of 1,3,4,6,7,8-hexahydro-4,6,6,7,8,8-hexamethylcycloenta[G]-2-benzopyran. The peak indicated by reference numeral 11 is for the n-hexane reaction solvent.

Referring to FIG. 1A the peak indicated by reference numeral 10 is for the mixture of diastereomers of 1,3,4,6,7,8-hexahydro-4,6,6,7,8,8-hexamethylcyclopenta[G]-2-benzopyran.

The peaks indicated by reference numerals 12A and 12B are for the mixtures of diastereomers of: 1,3,4,6,7,8-hexahydro-6-ethyl-4,6,8,8-tetramethylcyclo-penta[G]-2-benzopyran and 1,3,4,6,7,8-hexahydro-8-ethyl-4,6,6,8-tetramethyl-cyclo-penta[G]-2-benzopyran.

The peaks indicated by reference numerals 13A and 13B are for the mixtures of diastereomers of 1,3,4,7,8,9-hexahydro-7-ethyl-4,7,9,9-tetramethylpentamethyl-cyclopenta[H]-2-benzopyran and 1,3,4,7,8,9-hexahydro-9-ethyl-4,7,7,9-tetra-methylpentamethylcyclopenta[H]-2-benzopyran.

The peaks indicated by reference numerals 14A and 14B are for the mixture of diastereomers of 1,2,4,7,8,9-hexahydro-1,7,7,8,9,9-hexamethylpentamethyl-cyclopenta[F]-2-benzopyran.

The peaks indicated by reference numerals 15A and 15B are for the mixture of diastereomers of 1,3,4,7,8,9-hexahydro-4,7,7,8,9,9-hexamethylpentamethyl-cyclopenta[H]-2-benzopyran.

The following examples are illustrative and the invention is to be considered restricted thereto only as indicated in the appended claims. All parts and percentages given herein are by weight unless otherwise specified.

EXAMPLE I

Preparation of Solid Phase Benzopyran Composition 750 grams of the liquid phase benzopyran mixture was prepared according to Example 15 of U.S. Pat. No. 3,360,530, the specification of which is herein incorporated by reference, containing 78% by weight of 1,3,4,6,7,8-hexahydro-4,6,6,7,8,8-hexamethyl-cyclopenta[G]-2-benzopyran and 500 grams of hexane were admixed and cooled to a temperature of −30° C. with stirring. Stirring continued for a period of 1 hour at which point in time solid particles began to precipitate. The mixture was stirred for an additional 3 hours while slowly increasing the temperature of the benzopyran-solvent mixture to 0° C. The white solids were filtered at 0° C., resulting in the isolation of 240 grams of a mixture containing the following substances in the weight percentage stated:

(a) 88.6 weight % of 1,3,4,6,7,8-hexahydro-4,6,6,7,8,8-hexamethylcyclopenta[G]-2-benzopyran;

(b) 2.75 weight % of 1,3,4,6,7,8-hexahydro-6-ethyl-4,6,8,8-tetramethylcyclo-penta[G]-2-benzopyran;
(c) 2.75 weight % of 1,3,4,6,7,8-hexahydro-8-ethyl-4,6,6,8-tetramethylcyclo-penta[G]-2-benzopyran;
(d) 0.5 weight % of 1,3,4,7,8,9-hexahydro-7-ethyl-4,7,9,9-tetramethylpentamethyl-cyclopenta[H]-2-benzopyran and 1,3,4,7,8,9-hexahydro-9-ethyl-4,7,7,9-tetramethylpentamethylcyclopenta[H]-2-benzopyran;
(e) 4.0 weight % of 1,2,4,7,8,9-hexahydro-1,7,7,8,9,9-hexamethylpentamethyl-cyclopenta[F]-2-benzopyran; and
(f) 1.3 weight % of 1,3,4,7,8,9-hexahydro-4,7,7,8,9,9-hexamethylpentamethyl-cyclopenta[H]-2-benzopyran.

EXAMPLE II

Preparation of Solid Phase Benzopyran Composition 200 grams of the liquid phase benzopyran mixture was prepared according to Example 15 of U.S. Pat. No. 3,360,530 containing 78% by weight of 1,3,4,6,7,8-hexahydro-4,6,6,7,8,8-hexamethyl-cyclopenta[G]-2-benzopyran and 100 grams of 10% aqueous ethanol were admixed and cooled to a temperature of +5° C. with stirring. Stirring continued for a period of 2 hours at which point in time solid particles began to precipitate. The mixture was stirred for an additional 3 hours at 5° C. 42 grams of white crystalline material were filtered at 5° C. The resulting composition was a solid phase benzopyran mixture containing 91 weight % of 1,3,4,6,7,8-hexahydro-4,6,6,7,8,8-hexamethylcyclopenta[G]-2-benzopyran having a melting point of 31° C.

EXAMPLE III

Musk Perfume Compositions

The following musk perfume formulations were prepared:

| Ingredient | Example III(A)-parts by weight | Example III(B)-parts by weight |
|---|---|---|
| musk ambrette | 200 | 200 |
| musk ketone | 200 | 200 |
| beta ionone | 50 | 50 |
| vetiveryl acetate | 50 | 50 |
| sandalwood oil, E.I. | 100 | 100 |
| β-damascone | 80 | 80 |
| solid phase benzopyran composition of Example I | 10 | 0 |
| solid phase benzopyran composition of Example II | 0 | 10 |

The solid phase benzopyran compositions of Example I and II each imparted to this musk formulation a natural, sweet, musk, rose aroma with animalic topnotes and with great intensity and substantivity and each composition blended well with the formulation without any need for the use of any solvent.

EXAMPLE IV

Preparation of Soap Composition 100 grams of soap chips were admixed with 1 gram of each of the perfume compositions of Table I below until a substantially homogeneous composition was obtained. The perfumed soap manifested an excellent aroma as set forth in Table I below:

TABLE I

| Perfume Ingredient | Aroma |
|---|---|
| Solid Phase Benzopyran Composition of Example I | Musk, animalic aroma |
| Solid Phase Benzopyran Composition of Example II | Musk, animalic aroma |
| Perfume Composition of Example III(A) | Musk aroma with sweet musky, rose undertones and animalic topnotes |
| Perfume Composition of Example III(B) | Musk aroma with sweet musky, rose undertones and animalic topnotes |

EXAMPLE V

Preparation of a Cologne and Handkerchief Perfume

Each of the perfume substances as set forth in Table I of Example IV, supra, was incorporated into colognes at concentrations of 2.5%, 3.0%, 3.5% and 4.0% in 80%, 85%, 90% and 95% aqueous ethanol, and into handkerchief perfumes at concentrations of 15%, 20%, 25% and 30% in 85%, 90% and 95% aqueous ethanol. Distinct fragrances as set forth in Table I of Example IV were imparted to each of the cologne preparations and to each of the handkerchief perfume preparations at each of the levels indicated.

What is claimed is:
1. A solid phase benzopyran composition consisting of:
from about 85 weight % up to about 95 weight % of 1,3,4,6,7,8-hexahydro-4,6,6,7,8,8-hexamethylcyclopenta[G]-2-benzopyran;
from about 2.5 weight % up to about 5.5 weight % of 1,3,4,6,7,8-hexahydro-6-ethyl-4,6,8,8-tetramethylcyclopenta[G]-2-benzopyran;
from about 2.5 weight % up to about 5.5 weight % of 1,3,4,6,7,8-hexahydro-8-ethyl-4,6,6,8-tetramethylcyclopenta[G]-2-benzopyran;
from about 0.2 weight % up to about 0.5 weight % of 1,3,4,7,8,9-hexahydro-7-ethyl-4,7,9,9-tetramethylpentamethylcyclopenta[H]-2-benzopyran;
from about 0.2 weight % up to about 0.5 weight % of 1,3,4,7,8,9-hexahydro-9-ethyl-4,7,7,9-tetramethylpentamethylcyclopenta[H]-2-benzopyran;
from about 2.2 weight % up to about 4.0 weight % of 1,2,4,7,8,9-hexahydro-1,7,7,8,9,9-hexamethylpentamethylcyclopenta[F]-2-benzopyran; and
from about 0.7 weight % up to about 1.3 weight % of 1,3,4,7,8,9-hexahydro-4,7,7,8,9,9-hexamethylpentamethylcyclopenta[H]-2-benzopyran.
2. A process for augmenting, enhancing, or imparting an aroma in or to a consumable material selected from the group consisting of perfumed articles, perfume compositions, colognes and perfumed polymers comprising the step of admixing with said consumable material an aroma imparting, augmenting or enhancing quantity and concentration of the composition defined according to claim 1.
3. The composition of claim 1 having a melting point at 1 atmosphere absolute pressure of 34° C.
4. A process for preparing the solid phase benzopyran composition of claim 1 comprising the steps of:
i. admixing a liquid phase benzopyran composition consisting essentially of from about 70 weight % up to about

81 weight % of 1,3,4,6,7,8-hexahydro-4,6,6,7,8,8-hexamethylcyclopenta[G]-2-benzopyran;

from about 4 weight % up to about 10 weight % of the mixture of compounds (a) 1,3,4,6,7,8-hexahydro-6-ethyl-4,6,8,8-tetramethylcyclopenta[G]-2-benzopyran and (b) 1,3,4,6,7,8-hexahydro-8-ethyl-4,6,6,8-tetramethylcyclopenta[G]-2-benzopyran;

from about 1 weight % up to about 4 weight % of the mixture of the compounds (a) 1,3,4,7,8,9-hexahydro-7-ethyl-4,7,9,9-tetramethylpentamethylcyclopenta[H]-2-benzopyran and (b) 1,3,4,7,8,9-hexahydro-9-ethyl-4,7,7,9-tetramethylpentamethyl-cyclopenta[H]-2-benzopyran;

from about 2 weight % up to about 5 weight % of the compound, 1,2,4,7,8,9-hexahydro-1,7,7,8,9,9-hexamethylpentamethylcyclopenta[F]-2-benzopyran; and from about 2 weight % up to about 5 weight % of the compound, 1,3,4,7,8,9-hexahydro-4,7,7,8,9,9-hexamethylpentamethylcyclopenta[H]-2-benzopyran with a solvent selected from the group consisting of $C_4$-$C_{10}$ hydrocarbons, lower alkanols, lower dialkyl ketones, lower alkyl lower alkanoates, di-lower alkyl ethers and lower cyloaliphatic ethers, the weight percent range of said solvent being from about 20% by weight up to about 80% by weight of said liquid phase benzopyran mixture, thereby forming a liquid phase benzopyran-solvent mixture;

ii. adjusting the temperature of said liquid phase benzopyran-solvent mixture to a temperature in the range of from about −40° C. up to about 0° C. for a solid product-precipitating period of time thereby forming a mixture of solid phase benzopyran composition and liquid phase benzopyran-solvent mixture, and then iii. separating said solid phase benzopyran composition from said liquid phase benzopyran-solvent mixture.

5. A process for preparing the solid phase benzopyran composition of claim 1 comprising the steps of:

i. admixing a liquid phase benzopyran composition consisting essentially of from about 70 weight % up to about 81 weight % of 1,3,4,6,7,8-hexahydro-4,6,6,7,8,8-hexamethylcyclopenta[G]-2-benzopyran;

from about 4 weight % up to about 10 weight % of the mixture of compounds (a) 1,3,4,6,7,8-hexahydro-6-ethyl-4,6,8,8-tetramethylcyclopenta[G]-2-benzopyran and (b) 1,3,4,6,7,8-hexahydro-8-ethyl-4,6,6,8-tetramethylcyclopenta[G]-2-benzopyran;

from about 1 weight % up to about 4 weight % of the mixture of the compounds (a) 1,3,4,7,8,9-hexahydro-7-ethyl-4,7,9,9-tetramethylpentamethylcyclopenta[H]-2-benzopyran and (b) 1,3,4,7,8,9-hexahydro-9-ethyl-4,7,7,9-tetramethylpentamethylcyclopenta[H]-2-benzopyran;

from about 2 weight % up to about 5 weight % of the compound, 1,2,4,7,8,9-hexahydro-1,7,7,8,9,9-hexamethylpentamethylcyclopenta[F]-2-benzopyran; and from about 2 weight % up to about 5 weight % of the compound, 1,3,4,7,8,9-hexahydro-4,7,7,8,9,9-hexamethylpentamethylcyclopenta[H]-2-benzopyran;

with an aqueous solvent containing from about 2% up to about 20% by weight of water and from about 80% up to about 98% by weight of an organic solvent component selected from the group consisting of lower alkanols, lower dialkyl ketones, lower alkyl lower alkanoates, diethyl ether and tetrahydrofuran, the weight percent range of said aqueous solvent being from about 20% by weight up to about 80% by weight of said liquid phase benzopyran mixture, thereby forming a liquid phase benzopyran-aqueous solvent mixture;

ii. adjusting the temperature of said liquid phase benzopyran-aqueous solvent mixture to a temperature in the range of from about −10° C. up to about 25° C. for a solid product-precipitating period of time thereby forming a mixture of solid phase benzopyran composition and liquid phase benzopyran-aqueous solvent mixture, and then iii. separating said solid phase benzopyran composition from said liquid phase benzopyran-aqueous solvent mixture.

6. The process of claim 4, wherein the step of separating said solid phase benzopyran composition from said liquid phase benzopyran-solvent mixture is carried out by means of filtration.

7. The process of claim 5, wherein the step of separating said solid phase benzopyran composition from said liquid phase benzopyran-aqueous solvent mixture is carried out by means of filtration.

8. The process of claim 4, wherein the solvent admixed with the liquid phase benzopyran composition is n-hexane.

9. The process of claim 5, wherein the solvent admixed with the liquid phase benzopyran composition is 10% aqueous ethanol.

* * * * *